(12) United States Patent
Laugharn, Jr. et al.

(10) Patent No.: US 6,448,065 B2
(45) Date of Patent: Sep. 10, 2002

(54) INTEGRATED SEQUENCING DEVICE

(75) Inventors: James A. Laugharn, Jr., Winchester; Robert A. Hess, Cambridge, both of MA (US)

(73) Assignee: BBI Bioseq. Inc., West Bridgewater, MA (US)

( * ) Notice: Subject to any disclaimer, the term of this patent is extended or adjusted under 35 U.S.C. 154(b) by 0 days.

(21) Appl. No.: 09/812,262

(22) Filed: Mar. 19, 2001

Related U.S. Application Data

(62) Division of application No. 08/903,615, filed on Jul. 30, 1997, now Pat. No. 6,245,506.

(51) Int. Cl.$^7$ .............................. C12M 1/34; C12Q 1/68; C12P 19/34; C07H 21/02; C07H 19/00

(52) U.S. Cl. ..................... 435/287.2; 435/6; 435/7.1; 435/91.1; 435/91.2; 435/283.1; 435/285.2; 536/22.1; 536/23.1; 536/24.3; 536/24.31; 536/24.32; 536/24.33

(58) Field of Search ............................. 435/6, 7.1, 91.1, 435/91.2, 283.1, 285.2, 287.2; 536/221, 23.1, 24.3, 24.31, 24.32, 24.37

(56) References Cited

U.S. PATENT DOCUMENTS

| | | | |
|---|---|---|---|
| 4,962,037 A | | 10/1990 | Jett et al. |
| 5,436,130 A | * | 7/1995 | Mathies et al. ................ 435/6 |
| 5,552,270 A | * | 9/1996 | Khrapko et al. ............... 435/6 |
| 5,622,824 A | | 4/1997 | Köster ........................... 435/5 |
| 5,869,240 A | | 2/1999 | Patterson et al. |
| 6,036,923 A | | 3/2000 | Laugharn et al. ........ 822/82.13 |

FOREIGN PATENT DOCUMENTS

| | | | |
|---|---|---|---|
| WO | WO96/27432 | * | 9/1996 |
| WO | WO9627432 | | 12/1996 |

OTHER PUBLICATIONS

Kostichka et al., High Speed Automated DNA Sequencing in Ultrathin Slab Gels, Bio/Technology, 10:78–81, 1992.
Johnson et al., "Nonisotopic DNA Detection System Employing Elastase and a Flurogenic Rhodamine Substrate," Analytical Chemistry, 65:2352–2359, 1993.
Woolley et al., "Ultra–High–Speed DNA Sequencing Using Capillary Electrophoresis Chips," Analytical Chemistry 67:3676–3680, 1995.
Wilding et al., "PCR in a Silicon Microstructure," Clinical Chemistry, 40/9:1815–1818, 1994.
Lipshutz, et al., "Using Oligonucleotide Probe Arrays To Access Genetic Diversity," BioTechniques, 19/3:442–447, 1995.
FitzgeralD et al., "Mass Spectrometry of Nucleic Acids: The Promise of Matrix–Assisted Laser Desorption–Ionization (MALDI) Mass Spectrometry, "Annual Review of Biophysics and Biomolecular Structure, 24:117–140, 1995.
Wang et al., Rapid Sizing of Short Tandem Repeat Alleles Using Capillary Electrophoresis and Energy–Transfer Fluorescent Primers, Analytical Biochemistry, 67:1197–1203, 1995.
Pease et al., Light–generated Oligonucleotide Arrays for Rapid DNA Sequence Analysis, Proceedings of the national Academy of Sciences, 91:55022–5026, 1994.
Eggers et al., A Microchip for Quantitative Detection of molecules Utilizing Luminescent and Radioisotope Reporter Groups, Biotechniques, 17:516–523, 1994.
Mathies et al., "Capillary Array Electrophoresis: An Approach to High Speed, High–Throughput DNA Sequencing," Nature, 359:167–169, 1992.
Collins et al., "A New Five–Year Plan for the U.S. Human Genome Project", Science, 262:43–46, 1993.
Fleishmann et al., "Whole–Genome Random Sequencing and Assembly of Haemophilus influenzae Rd," Science, 269:296–298, 1995.
Woolley et al., "Ultra–High Speed DNA Fragment SeparationS Using Microfabricated Capillary Array Electrophoresis Chips," Proceedings of the National Academy of Sciences, 91:11348–11352, 1994.
Walker et al., "Multiplex Strand Displacement Amplification (SDA) and Detection of DNA Sequencing From MYcobacterium tuberculosis and Other Mycobacteria," Nucleic Acids Research, 22:2670–2677, 1994.
Nikiforov et al., "Genetic Bit Analysis: A Solid Phase Method for Typing Single Nucleotide Polymorphisms," Nucleic Acids Research, 22:4167–4175, 1994.
Fraser et al., "The Minimal Gene Complement of Mycoplasma genitalium," Science, 270:397–403, 1995.
Schena et al., "Quantitative Monitoring of Gene Expression Patterns with a Complementary DNA Microarray," Science, 270–467–470, 1995.

(List continued on next page.)

Primary Examiner—Jeffrey Siew
(74) Attorney, Agent, or Firm—Fish & Richardson P.C.

(57) ABSTRACT

The invention is based on the discovery that the sequence of monomers in a polymeric biomolecule can be determined in a self-contained, high pressure reaction and detection apparatus, without the need for fluid flow into or out from the apparatus. The pressure is used to control the activity of enzymes that digest the polymeric biomolecule to yield the individual monomers in the sequence in which they existed in the polymer. High pressures modulate enzyme kinetics by reversibly inhibiting those enzymatic processes which result in a higher average activation volume, when compared to the ground state, and reversibly accelerating those processes which have lower activation volumes than the ground state. Modulating the pressure allows the experimenter to precisely control the activity of the enzyme. Conditions can be found, for example, where the enzyme removes only one monomer (e.g., a nucleotide or amino acid) from the biomolecule before the pressure is again raised to a prohibitive level. The identity of the single released nucleotide or amino acid can be determined using a detector that is in communication with a probe in the detection zone within the reaction vessel.

2 Claims, 5 Drawing Sheets

OTHER PUBLICATIONS

Chadwick et al., "Heterozygote and Mutation Detection by Direct Automated Fluorescent DNA Sequencing Using a Mutant Taq DNA Polymerase," BioTechniques, 20:676–683, 1996.

Fodor et al, "Multiplexed Biochemical Assays with Biological Chips," Nature, 364:555–556, 1993.

Tabor et al., "A Single Residue in DNA Polymerases of the *Escherichia coli* DNA Polymerase I Family is Critical for Distinguishing Between Deoxy– and Dideoxyribonucleotides," Proceedings of the National Academy of Sciences, 93:6339–6343, 1995.

O'Neill, "Sequences Benefit from Solid–State Detectors," Laser Focus World, 135–142, 1995.

Fitzgerald et al., "The Analysis of Mock DNA Sequencing Reactions Using Matrix–assisted Laser Desorption/Ionization Mass Spectrometry," Rapid Communications in Mass Spectrometry, 7:895–897, 1993.

Shaler et al., "Analysis of Enzymatic DNA Sequencing Reactions by Matrix–assisted Laser Desorption/Ionization Time–of–flight Mass Spectrometry," Rapid Communications in Mass Spectrometry, 9:942–947, 1995.

Butler et al., "Application of Dual Internal Standards for Precise Sizing of Polymerase chain Reaction Products Using Capillary Electrophoresis," Electrophoresis, 16:974–980, 1995.

Jacobson et al., "Microchip Electrophoresis with Sample Stacking," Electrophoresis, 16:481–486, 1995.

Lipshutz et al., "Advanced DNA Sequencing Technologies," Current Opinion in Structural Biology, 4:376–380, 1994.

Matson et al., "Biopolymer Synthesis on Polypropylene Supports: Oligonucleotide Arrays," Analytical Biochemistry, 224:110–116, 1995

Huang et al., "Capillary Array Electrophoresis Using Laser--Excited Confocal Fluorescence Detection," Analytical Chemistry, 64:967–972, 1992.

Reeve et al., "A Novel Thermostable Polymerase for DNA Sequencing," Nature, 376:796–797, 1995.

Eggers et al., "Review of Microfabricated Devices for Gene–Based Diagnostics," Hematologic Pathology, 9:1–15, 1995.

Hasan et al. Tetrahedron vol. 53, No. 12 pp. 4247–4264, 1997.

Whittal et al. Anal. Chem vol. 67 pp. 1950–1954, 1995.

* cited by examiner

INTEGRATED SEQUENCING DEVICE

This application is a division of U.S. application Ser. No. 08/903,615, filed Jul. 30, 1997, now U.S. Pat. No. 6,245,506, Jun. 12, 2001.

BACKGROUND OF THE INVENTION

The invention is in the field of devices and methods for sequencing biopolymers.

The prevailing DNA sequencing methods are based on Sanger chemistry and on fragment analysis using gel-based electrophoresis. These methods reveal the base pair sequence of individual fragments of DNA. The bases are separated by subjecting the fragments, suspended in a slab gel, to an electrical field. This causes size-dependent migration and spatial separation of the fragments. Once they have been separated on the gel, the bands corresponding to the individual base pairs are read or digitally scanned to determine the fragment sequence.

Although the results obtained from gel electrophoresis are generally of high quality and reliability, the process is labor intensive and relatively slow. Due to its complexity, gel electrophoresis often requires a skilled technician. Additionally, preparing samples prior to sequencing requires that the target be isolated, purified, amplified, and fragmented into relatively smaller pieces (e.g., about 300 to 500 base pairs). Since the average length of a human gene is over 50,000 bases (i.e., 15,000 to over 1,000,000 bases), considerable sample preparation is necessary to systematically fragment, purify, and amplify the fragments.

To ensure that each fragment is sequenced at least once, the target section is often deliberately overlapped, with the consequence that the same bases may be sequenced ten times or more in the end. Once the sequencing has been completed, the resulting data are processed to deduce the sequence of the original target section.

Improved engineering and automation have resulted in sequencing systems that include such technological advances as automated gel-based electrophoresis or ultra-thin capillary tube electrophoresis. These techniques permit higher speed and lower cost sequencing but are still limited by the fundamental constraints of Sanger-based chemistry and fragment analysis, namely the need for highly trained personnel to prepare relatively short read lengths. Nonetheless, automated gel electrophoresis is the technique currently used for almost all high throughput commercial sequencing.

Current efforts toward gene discovery, for example those based on "population-based" genetic analysis, can create tremendous demand for cost-effective DNA sequence analysis. For example, HIV protease inhibitor medications recently introduced rely heavily on DNA sequencing of individual patient samples to detect the emergence of resistant strains of HIV and subsequently alter choice of therapeutic intervention. Indeed, cost-effective DNA sequence analysis methods are likely to prove to be a prerequisite for "individual-based" preclinical and clinical patient studies.

SUMMARY OF THE INVENTION

The invention is based on the discovery that the sequence of monomers in a polymeric biomolecule can be determined in a self-contained, high pressure reaction and detection apparatus, without the need for fluid flow into or out from the apparatus. The pressure is used to control the activity of enzymes that digest the polymeric biomolecule to yield the individual monomers in the sequence in which they existed in the polymer. High pressures modulate enzyme kinetics by reversibly inhibiting those enzymatic processes which result in a higher average activation volume, when compared to the ground state, and reversibly accelerating those processes which have lower activation volumes than the ground state. Modulating the pressure allows the experimenter to precisely control the activity of the enzyme. Conditions can be found, for example, where the enzyme removes only one monomer (e.g., a nucleotide or amino acid) from the biomolecule before the pressure is again raised to a prohibitive level. The identity of the single released nucleotide or amino acid can be determined using a detector that is in communication with a probe in the detection zone within the reaction vessel.

In general, the invention features an integrated device for sequencing a polymeric biomolecule, including: a reaction vessel that includes a reaction zone and a detection zone; a solid support in the reaction zone for chemical attachment of the polymeric biomolecule; an enzyme that catalyzes the removal of one monomer unit at a time from one end of the polymeric biomolecule; a probe for sensing a characteristic (e.g., fluorescence, mass, impedance, optical, voltammetric or amperometric properties, etc.) of the released monomers positioned within the detection zone of the reaction vessel; and a pressure-control device (e.g., piezoelectric crystal-driven pressure modulation, thin-film-driven pressure modulation, electronic, pneumatic, hydraulic, magnetostrictive, etc.) that controls the pressure at least in the reaction zone of the reaction vessel.

Solid supports are available in many configurations, including beads, filters, membranes, capillaries, and frits. Both organic and inorganic supports can be used. For example, sephadex, agarose, dextran, latex, silica gel, glass, polyacrylamide, polystyrene, polyethylene, polyvinylidenefluoride, and other polymers; collagen and similar gels; and biological substrates can all be suitable.

The solid supports can be activated to form specific bonds with biomolecules. Reagents used to activate the solid supports toward covalent bonding include the cyanogen halides, sulfonyl chloride, periodates, sulfonate glutaraldehyde, and carboxyl functionalized compounds.

The reaction zone can be either spatially separated from the detection zone or not.

The probe can be an optical window of quartz or sapphire.

The device can also include a modulated electrophoretic, electroosmotic, fluid flow, or flow cytometry device to connect the reaction and detection zones. The modulation device can contain a buffer, the pH of which is pressure-sensitive.

The device can include multiple probes within its detection zone, allowing it to sense a characteristic of a multiplicity of monomers (e.g., for parallel analysis of multiple single molecule sequencing reactions).

The probe can be, for example, an optical fiber for fluorescence detection, a fluorescence microscope (e.g., CCD-based or confocal), an infrared or Raman spectrometer, a fluorescence polarimeter, an enzymatic biosensor, or a mass spectrometer.

The polymeric biomolecule can be a nucleic acid or a polypeptide, for example.

At least some of the monomers of the polymeric biomolecule can be labelled with fluorescent tags, and the identity of the fluorescently labelled monomers can then be determined by fluorescence resonance energy transfer between the monomers and the enzyme.

Another embodiment of the invention is a sample plate that includes a solid surface adapted for use in the sequencing device described above, and a linker molecule covalently bonded to the surface and to a primer molecule complementary to a biomolecule to be sequenced.

Still another embodiment of the invention features a method for sequencing a polymeric biomolecule. The method includes the steps of immobilizing the polymeric biomolecule on a solid support in a reaction vessel; associating an iondependent, biomolecule-digesting enzyme with the nucleic acid under conditions in which the activity of the enzyme is blocked by an exogenously controllable characteristic that can be altered without adding a reagent from a separate vessel; then, with the pressure in the vessel at a level that inactivates the enzyme, altering the exogenously controllable characteristic to allow the enzyme's biomolecule digesting activity to be functional and to excise the terminal monomer from the polymeric biomolecule; adjusting the pressure to activate the enzyme to dissociate one monomer from the polymeric biomolecule; determining the identity of the dissociated terminal monomer with a probe for sensing a characteristic of the dissociated monomer within the reaction vessel; adjusting the pressure to inactivate the enzyme; and repeating the pressure adjusting and identity determining steps. The biomolecule immobilizing and enzyme associating steps can be performed in either order, so long as they precede the characteristic altering step.

The polymeric biomolecule can be either a nucleic acid molecule (e.g., DNA or RNA) or a polypeptide, for example. The enzyme can thus be an exonuclease or an exopeptidase (e.g., carboxypeptidase C), respectively.

The exogenously controllable characteristic can be ion concentration (e.g., $Mg^{2+}$, $Mn^{2+}$, $Co^{2+}$, $Cr^{3+}$, $K^+$, $Zn^{2+}$, or ethylenediamine$^{2+}$concentration), pH, or a photolabile protecting group, for example. Such a photolabile protecting group can be attached to either the enzyme or the polymeric biomolecule, or can be a cage-like chelating molecule that sequesters divalent metal ions necessary for the enzyme's biomolecule digesting activity. The photolabile protecting group can be removed by an intense pulse of light.

Examples of photolabile protecting groups include, but are not limited to: 4,5-dimethoxy-2-nitrobenzyl bromide or trans-2-(4,5-dimethoxy-2-nitrophenyl)-1-nitroethene (suitable if the enzyme contains a catalytically important thiol); 1-(4,5-dimethoxy-2-nitrophenyl)ethyl (DMPNE) (suitable if the enzyme or the biomolecule contains a catalytically important carboxylate); NVOC chloride (suitable if the enzyme contains a catalytically important amine); or 1-(4,5-dimethoxy-2-nitrophenyl) EDTA (suitable for sequestering magnesium ions.

Ion concentration (e.g., $[Mg^{++}]$) and pH can be altered by a pressure change, through the use of buffers with high absolute ionization volumes (e.g., borate, 1,3-"bis-tris" propane, pyrophosphate ion, etc.), for example, electronically, or by an intense pulse of light. Depending on the enzyme being used, a pH in the range of 3 to 11 can be permissive. Magnesium ion concentrations of 0.1 to 50 mM are often suitable.

The polymeric biomolecule and the solid support can both be in the organic phase of a biphasic solvent system, while the dissociated monomers are detected in the aqueous phase of the biphasic solvent system.

pH can also be altered by the release of a proton from 2-hydroxyphenyl-1-(2-nitrophenyl)ethyl phosphate.

The monomers can be labelled with fluorescent tags to facilitate identification. In some instances, the identity of the fluorescently labelled monomers are discriminated by fluorescent resonance energy transfer between the monomers and the enzyme. For example, the inherent fluorescence of the enzyme can be the energy donor and the fluorescently labelled monomers can be the energy acceptors. Alternatively, the enzyme can be derivatized with a fluorescent label and can thereafter act as the energy donor or acceptor.

The dissociated monomer can also be transported from the reaction site to a detection zone (e.g., 1 μm to 1 mm away, or further) within the reaction vessel. This transporting step can be effected by intermittent electrophoresis, electroosmosis, fluid flow, or flow cytometry. A gel can be used, although it is not necessary.

The dissociated monomer can be detected at the reaction site.

The pressure can be modulated using feedback from the probe or another detection device.

A detection device relies on pH titration of the spectroscopic or electrophoretic properties of labelled or unlabelled adenosine monophosphate, guanosine monophosphate, cytidine monophosphate, and thymidine monophosphate.

The pressure can be increased to a level sufficient to allow direct identification of the dissociated nucleic acid monomer by inherent fluorescence properties in organic solvent, for example.

A pulsed current can be used to induce the activity of the enzyme, or a continuous current can be supplied to extend and relax polymeric biomolecule binding to facilitate enzyme activity. For example, strands of DNA can be straightened by electricity (or by exposure to organic solvent or flowing aqueous solvent).

A fluorophore can be introduced to allow indirect detection of monomer absorbance properties.

The solid support can be a plate. The size of the plate depends on the sensitivity of the probe, and whether the sequencing is carried out in a parallel (i.e., multiple probes) or in a serial manner. The plate can be made from various materials (e.g., glass, metal, semiconductor, insulator, polymer, etc.). The plates can be either disposable or reusable. The pressure exerted in the vicinity of the plate (or in other locations within the reaction vessel) can be the same as the pressure throughout the entire vessel or can be generated locally. For example, a magnetostrictive (i.e., elastic deformation of a ferromagnetic material such as nickel upon application of a magnetizing force, quartz crystal, a ceramic transducer, or an ultrasonic (>20 kHz) transducer) device can be used; local pressure changes can also be effected with a piezoelectric device, wherein a mechanical deformation occurs, produced by the interaction of an applied electric field with an anisotropic crystal. Localized pressure allows, for example, the reaction vessel to be in communication with other vessels at enzyme operative pressures. The plate can be a microfabricated or micromachined circuit (suitable if electrophoresis is used).

The enzyme can have a net neutral charge, either naturally or due to a mutation. In some cases, the enzyme is not metal ion-dependent. For example, the enzyme can be an acid exonuclease, or a phosphodiesterase (e.g., snake venom phosphodiesterase). A continuous supply of metal ions (e.g., divalent magnesium ions) can be introduced the reaction zone in some cases.

Many classes of nucleases can be used in the new devices and methods. Examples include the 3'-exonucleases such as snake venom phosphodiesterase and *E. coli* exonucleases VII (EC 3.1.11.6) and III (EC 3.1.11.2), λ-exonuclease (EC 3.1.11.3), T7 Gene 6 exonuclease, and the exonuclease activities of certain polymerases (e.g., T4, Taq, Deep Vent, and Vent DNA polymerases) or subunits of polymerases (e.g., T7 subunit of DNA polymerase III of *E. coli*). Other enzymes useful in sequencing include mung bean nuclease, Bal-31 exonuclease, S1 nuclease, *S. aureus* micrococcal nuclease, DNase I, and other exodeoxyribonucleases producing 5'-phosphomonoesters (EC 3.1.11.X; X can be any integer corresponding to a known enzyme).

For sequencing RNA, ribonuclease A and T1 micrococcal nuclease are suitable. Other exoribonucleases (EC 3.1.13.X and 3.1.14.X) and exonucleases active with either DNA or RNA (EC 3.1.15.X and 3.1.16.X) can also be used.

For sequencing polypeptides, suitable peptidases include: exopeptidases, carboxypeptidases A, B, and C (3.4.17.1, EC 3.4.17.2, and EC 3.4.16.1, respectively), serine-type carboxypeptidase C (EC 3.4.16.5), aminopeptidase M (EC 3.4.11.2) and other aminopeptidases (EC 3.4.11.X), dipeptidases (EC 3.4.13.X), dipeptidyl- and tripeptidylpeptidases (EC 3.4.14.X), peptidyl-dipeptidases (EC 3.4.15.X), serine-type carboxypeptidases (EC 3.4.16.X), metallocarboxypeptidases (EC 3.4.17.X), cysteine-type carboxypeptidases (EC 3.4.18.X), omega peptidases (EC 3.4.19.X), serine endopeptidases (EC 3.4.21.X), cysteine endopeptidases (EC 3.4.22.X), aspartic endopeptidases (EC 3.4.23.X), metalloendopeptidases (EC 3.4.24.X), and other endopeptidases of unknown catalytic mechanism (3.4.99.X).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, technical manuals, and other references mentioned herein are incorporated by reference in their entirety. In case of conflict, the present application, including definitions, will control. In addition, the materials, methods, and examples are illustrative only and not intended to be limiting.

An advantage of the new devices and methods is the capability to rapidly and economically sequence nucleic acid molecules or polypeptides in a single apparatus. Because the devices require only pressure modulation to control, digest, separate, and analyze, there is no need for hazardous chemicals (e.g., acrylamide or cross-linking agents) to be used. Furthermore, no waste is generated other than the digestion products. By combining the reaction and detection functions in a single unit, the new devices and methods can also save time.

Another advantage is that the new devices and methods eliminate the need to add additional reagents to the reaction vessel under high pressure conditions. Still another advantage is that the new devices and methods utilize a probe within the detection zone of the reaction vessel, allowing detection at high pressure nearly concurrent with the digestion reactions.

Other features and advantages of the invention will be apparent from the following detailed description, and from the claims.

DETAILED DESCRIPTION OF THE INVENTION

A sequencing device can be based on the relationship between pressure and enzymatic activity. Exonucleases and exopeptidases are modifying enzymes that catalyze the hydrolytic cleavage of one nucleotide or amino acid residue at a time from the ends of nucleic acid molecules and polypeptides, respectively, regardless of the identity of the terminal nucleotide or amino acid or the overall sequence. Under hyperbaric conditions, exonucleases and exopeptidases are catalytically inactive. By decreasing and increasing the pressure at appropriate times (e.g., in a pressure cycling reactor), the enzyme can be controlled to react just once before the pressure is again altered to a prohibitive level. The released product can, for example, be removed from the reaction chamber (e.g., electrophoretically, electroosmotically, by fluid flow, or flow cytometry) and identified by standard analytical methods (e.g., optical sensing, impedance measurement, voltammetry, mass spectroscopy, or amperometry), or can be detected at the reaction site (e.g., by fluorescence resonance energy transfer).

General

Figure 1:
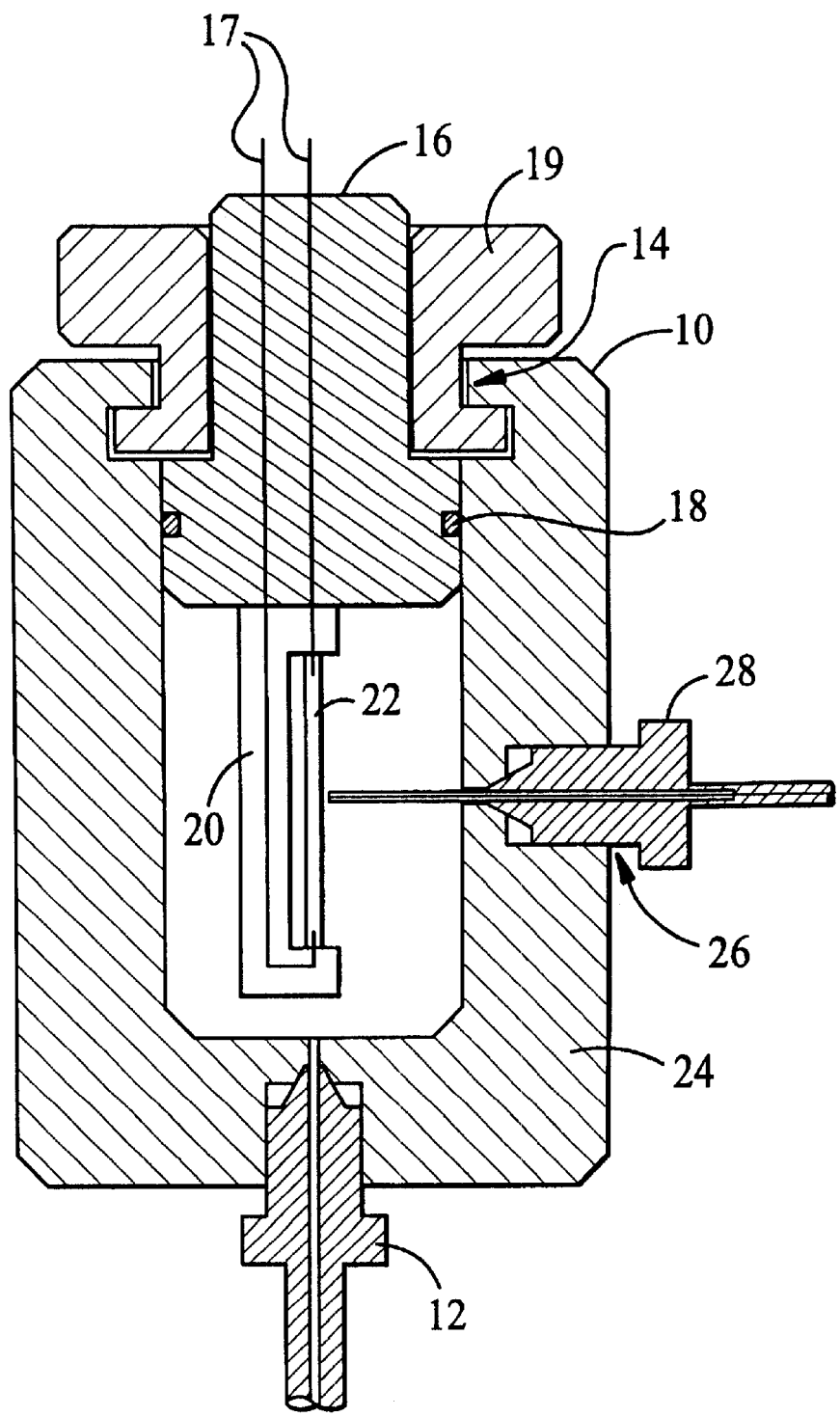
FIG. 1 is a cross-sectional view of a pressure cell.

FIG. 1 is a cross-sectional view of a pressure cell 10. The cell includes a bottom port 12, through which fluid under pressure is applied, and a top opening 14 with a radially sealed, removable cap 16. The cap 16 contains two sealed electrical feed-throughs 17 for applying an electrophoresis voltage, a seal 18, and a locking ring 19. The cap 16 also provides mounting means 20 for a reaction capillary 22. The sidewall 24 of the cell contains a threaded, pressure-sealed port 26 for receiving a fiber optic fitting 28.

Figure 2:
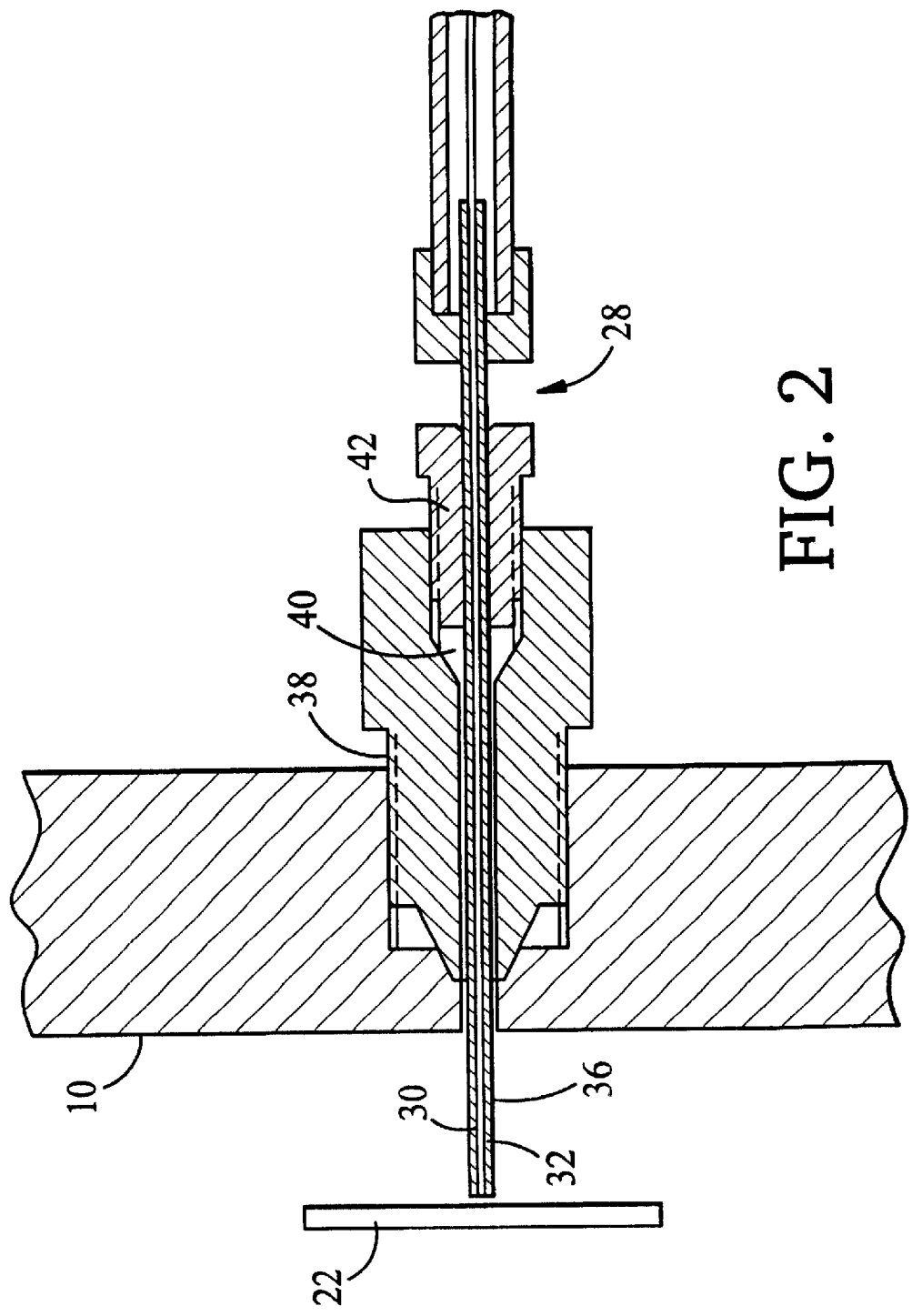
FIG. 2 is a cross-sectional view of a fiber optic fitting.

FIG. 2 presents a cross-sectional view of the fiber optic fitting 28. This fitting 28 contains and locates the end of an optical fiber 30 in close proximity to the reaction capillary 22. The fitting 28 also provides a seal 32 for the fiber 30 that is capable of withstanding the pressures within the pressure cell 10. This seal 32 is achieved by first epoxying the optical fiber 30 into a short length of stainless steel hypodermic tubing 36. This tubing 36 is, in turn, retained and sealed into a pressure fitting 38 by means of a ferrule 40 and ferrule nut 42.

Figure 3:
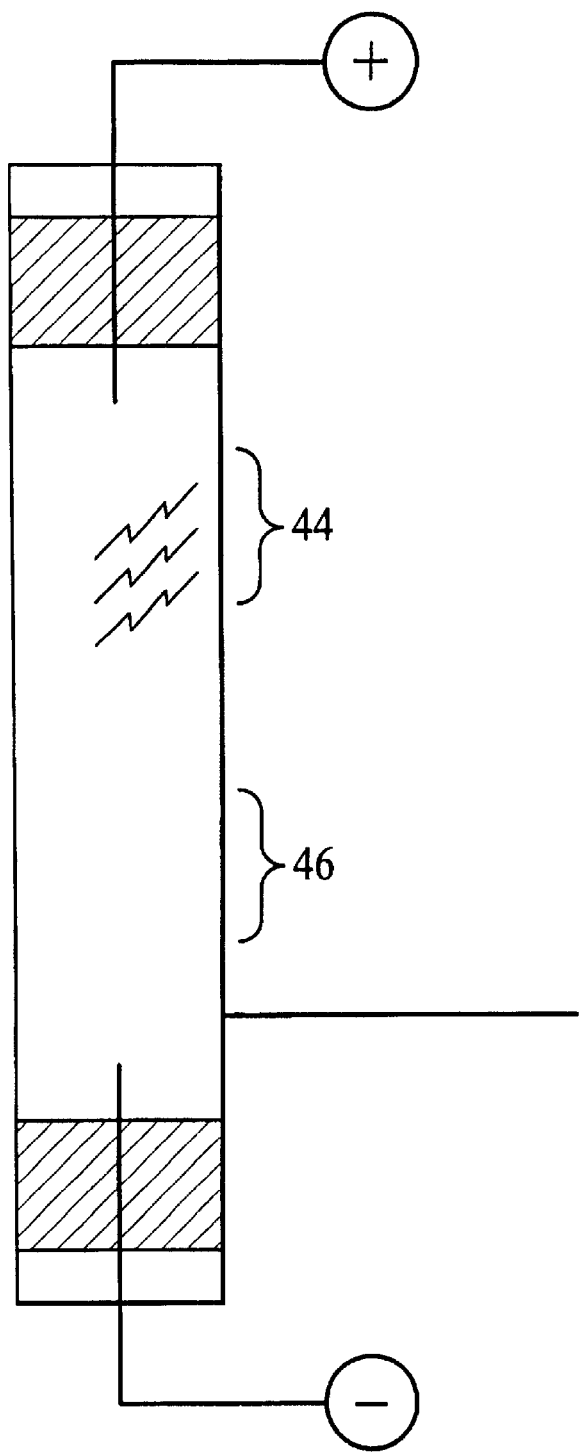
FIG. 3 is a cross-sectional view of a reaction zone and detection zone.

FIG. 3 is a cross-sectional view of the reaction zone 44 and the detection zone 46 of the pressure cell 10. The nucleotide monophosphates released from the reaction zone 44 are spatially separated from the reaction zone 44 and introduced into the detection zone 46. Means for spatial separation include, but are not limited to, electrophoresis, electroosmosis, and positive fluid displacement.

Figure 4A:
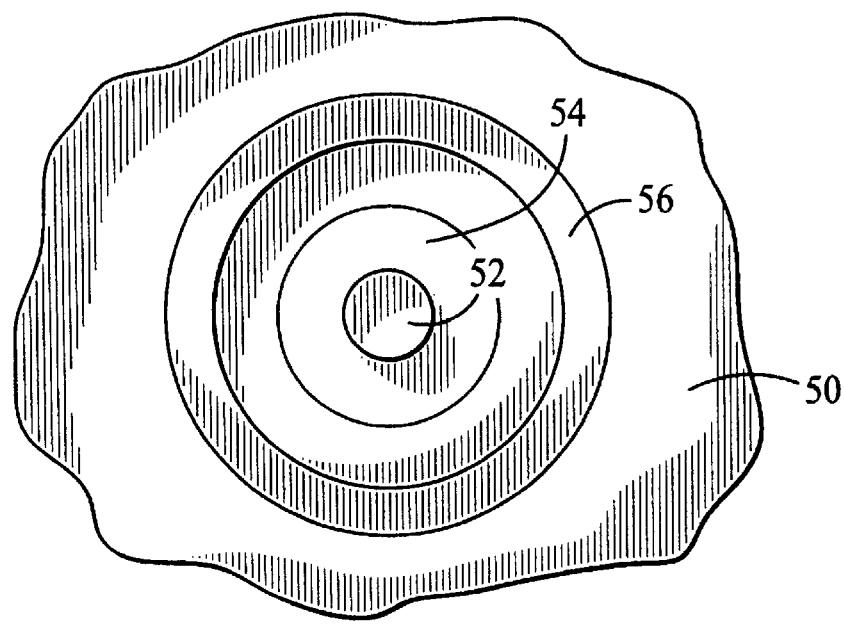
FIGS. 4A to 4C are views of a 25-well microchip for DNA sequencing.
Figure 4B:
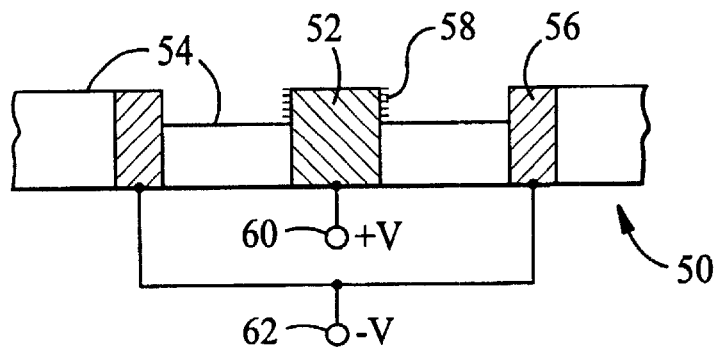
Figure 4C:
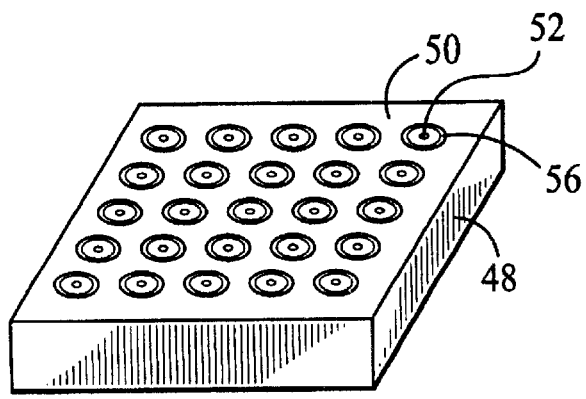

FIGS. 4A to 4C are views of a 25-well microchip 48 for DNA sequencing. Each well 50 includes a center electrode 52, surrounded by an electrically insulating material 54 that separates it from a ring shaped outer electrode 56. The exposed cylindrical surface 58 of the center electrode 52 is coated with an immobilized, fluorescently labelled DNA sample; during the sequencing procedure, the released nucleotide are transferred toward the outer electrode 56. All twenty-five center electrodes 52 are interconnected to a common conductor 60, and all outer electrodes 56 are similarly interconnected to a second common conductor 62. A voltage is applied between these conductors 60 and 62, which polarizes the center electrode 52 positively with respect to the outer electrode 56. In an alternative embodiment, the outer electrode 56 can be coated with the fluorescently labelled DNA sample; the released nucleotides would thus be drawn to the center electrode 52 during the sequencing reaction.

Figure 5:
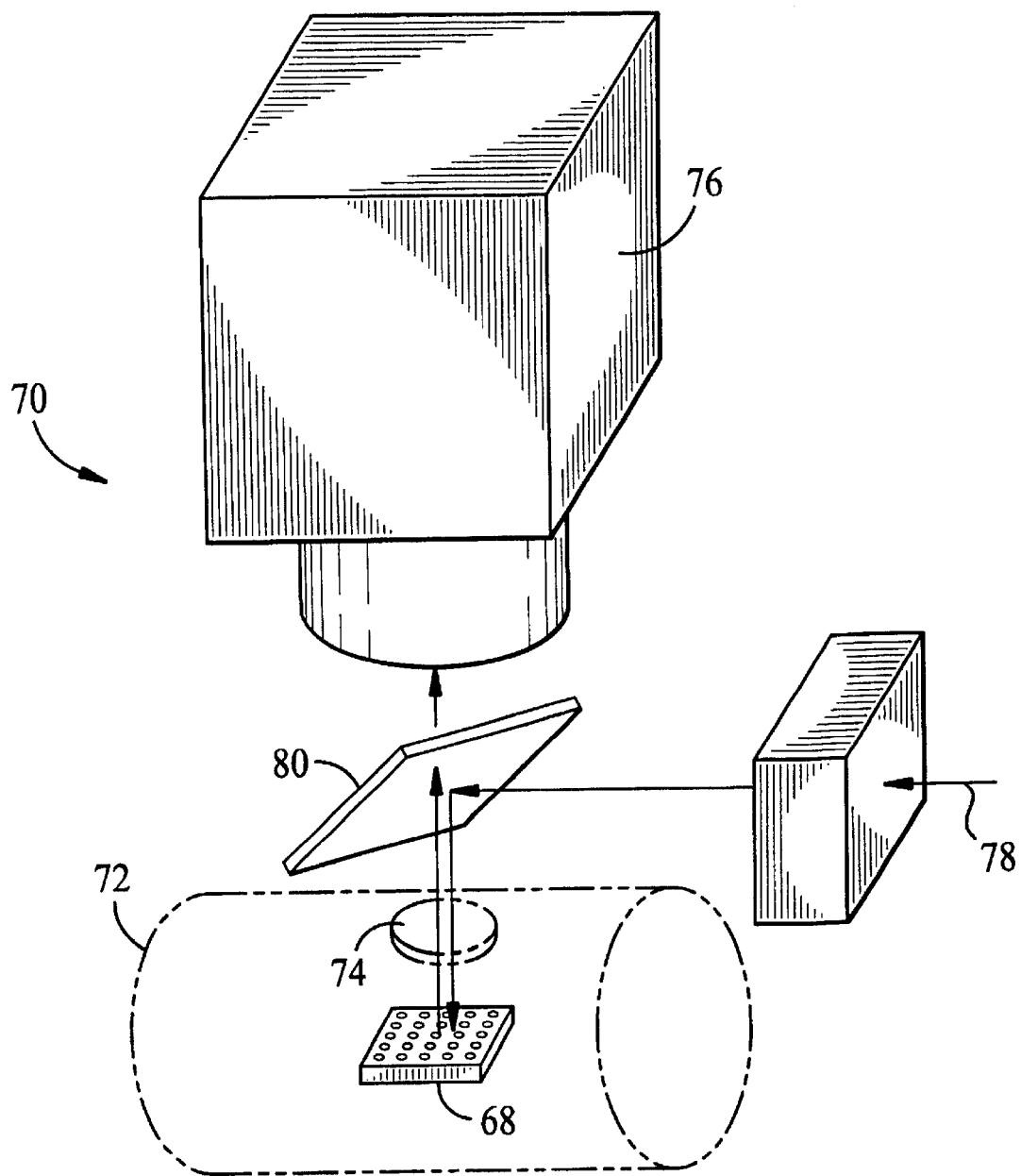
FIG. 5 is a view of an optical detection system.

FIG. 5 is a view of a microchip 68 for use in an optical detection system 70. The microchip 68 is enclosed within a pressure cell 72 containing an optical window 74. A CCD camera 76 is positioned so that it can view the entire chip 68 through the window 74. A laser beam 78 of the appropriate excitation wavelength is scanned across the entire chip 68 in a two-dimensional raster pattern at a frequency of several hundred Hz. The stationary dichroic mirror 80 is transparent to the camera 76 at the fluorescent emission wavelength, but provides a 90° deflection of the laser beam.

Nucleic Acid Sequencing

As exonucleases are highly processive (i.e., they are capable of uninterrupted association with their substrates over many cycles of reactions) and have very rapid reaction rates (e.g., 275 bases cleaved per second with *E. coli* exonuclease I), they are potentially powerful tools for DNA sequencing applications.

An advantage of the present method is the ability that it affords to sequence bulk amounts of DNA, thereby providing a strong signal. However, enforcement of synchronization of the population of enzymes in the sample is difficult and is nevertheless necessary for maintaining the correlation between polymer sequence and the time of signal detection.

In one embodiment, single molecule sequencing is used to improve synchronism. When there is only a single molecule involved, the digestion is inherently synchronous. One single molecule sequencing approach utilizes exonucleases to sequentially degrade native DNA and detect intrinsic fluorescence of unmodified nucleic acids. This approach requires physical separation and decoupling of the biological enzyme reaction at ambient temperature (310 K) from the native base detection at 111 K as the environments are mutually exclusive.

Another single molecule sequencing approach involves incorporating fluorescently tagged nucleotides into doublestrands using DNA polymerase and single strand templates. This tagging approach is currently being pursued by Los Alamos National Laboratories (U.S. Pat. No. 5,405,747) and a consortium formed by the Karolinska Institute. This method requires 100% dye-tagged nucleotide incorporation. Typically, however, only 0.1% to 40% of tagged molecules are incorporated in non-single molecule DNA polymerase sequencing reactions.

One method of compensating for the loss of synchronism is to run many single molecule reactions simultaneously (i.e., in parallel). The time-dependent release of nucleotides from parallel reactions can correlate well with the actual sequence, while facilitating detection with less sensitive equipment.

To improve the resolution by light microscopy in the analysis of the multiple single molecule reactions, a bulky adapter molecule can be used to achieve even spacing of the reactions on the solid support. Suitable adapter molecules include dendrimers, biotin/avidin complexes, and derivatized proteins. Detection can then be achieved, for example, by fluorescence resonance energy transfer or fluorescence polarization measurement.

In another embodiment, electrophoretic techniques can be adapted to increase signal-to-noise ratio. For example, negatively charged molecules are displaced by an electric field, whereas sources of background signals generally are not. Fluorescence correlation spectroscopy takes advantage of this fact, allowing exonuclease based sequencing methods to use very small amounts of fluorescent label, minimizing adverse effects attributable to steric crowding of highly labelled DNA. A fluctuating electric field in each microscopic sequencing unit can enable measurement of correlated fluctuations of emitted light. A circular, three-electrode system (see FIGS. 4A to 4C), for example, can allow electrical fluctuation with minor perturbation of the field around the DNA molecules.

Because of the circular electric field, individual nucleotide molecules will move in nearly random directions and correlated fluctuations can be measured using fluorescence microscopy in conjunction with a high resolution CCD-array camera (see FIG. 5) or an array of optical fibers.

A homogeneous DNA population can be obtained at the start of the sequencing procedure through the use of fill-in PCR in the 5'→3' direction. The sequence is read from 5'→3'.

The activation volumes for some enzymes that catalyze phosphodiester hydrolysis reactions are negative. For example, ribonuclease catalyzed hydrolysis of cytidine 2',3'-phosphate has an activation volume of −20+/−2 ml/mol (R. Williams and C. Shen, *Arch. Biochem. Biophys.* 152, 606612, 1972). Data shown here indicate a negative activation volume for the λ-exonuclease-catalyzed release of a single nucleotide. Pressure cycling can therefore synchronize the enzyme population, thereby providing precise control of DNA digestion by exonuclease. High pressure is thought to increase the rate of hydrolysis of individual nucleotides from the 5' ends of the DNA while simultaneously inhibiting the enzyme from advancing to the next base. Methods that further accelerate the hydrolysis reaction, such as modulation of pH during a defined phase of the pressure cycle, can be used to optimize the process.

Pressure can also be used to modulate enzyme activity by changing the concentration of free ions (e.g., $H^+$, $OH^-$, or $Mg^{++}$) in a reaction. For example, pressure can be used to shift the equilibrium of a buffer having a large ionization volume. For instance, pyrophosphate has been reported to have an ionization volume of −28.9 ml/mol for its pK 9.4 proton dissociation (Kitamura and Itoh, *J. Sol. Chem.* 16, 1987, 715). This corresponds to a pH decrease of about 1.5 units and a pOH increase of 0.5 units at 4 kbar of pressure. For a buffer with an ionization volume of +20/ml/mol, one expects a pH increase of about one unit in pH and a pOH decrease of over 2 units, corresponding to a 100 fold rate acceleration for a hydroxide catalyzed reaction. Enzymatic reactions can have even larger pH-dependent rate changes occurring at the titration points of one or more amino acid residues or cofactor moieties involved in catalytic activity.

Pressure modulated equilibrium shifts can be used to alter the concentrations of cofactors and inhibitors. For example a $Mg^{++}$/EDTA buffer system will have an increased free $Mg^{++}$ concentration under high pressure, thus stimulating the exonuclease. In another example, a pressure-induced change in the ionization of a polyamine compound would modulate the enzyme activity. Certain polyamine compounds are known to be inhibitory to DNA hydrolyzing enzymes due to the ability of the amino cations to tightly bind the DNA phosphate backbone.

Pressure modulated equilibrium shifts can also be used to alter the properties of solvents. For example, the polarity and hydrophilicity of a nonpolar organic solvent increases with pressure (*J. Am. Chem. Soc.*, 115, 8845–8846, 1993). Polarity changes can be used to modulate enzyme activity. Many enzymes retain activity in aqueous-organic biphasic solutions. For example, replacement of the "bulk" water solvent with an organic solvent does not completely inhibit the reactivity, provided that low concentrations of water are available to bind in a monolayer (or less) around the enzyme (*Biotransformations in Organic Chemistry*, K. Faber, 2$^{nd}$ Edition, Springer-Verlag, pp. 271-311, (1995). Additionally, using biphasic solutions in conjunction with pressure modulation can be advantageous for augmenting the spatial separation of the reaction components.

The device can employ biosensors, analytical devices that use the binding and catalytic properties of biopolymers such as enzymes, binding proteins, or oligonucleotides to detect an analyte in a mixture. Biosensors can transduce and amplify binding information into an optical or electrical signal. An integrated sequencing device can utilize specific enzyme-nucleotide interactions to discriminate among the four nucleoside monophosphates liberated by exonuclease action.

A class of enzymes that is useful for use in biosensors is the 5'-monophosphate kinases: cytidylate kinase (EC 2.7.3.14), dTMP kinase (EC 2.7.4.9), guanylate kinase (EC 2.7.4.8), and dAMP kinase (EC 2.7.4.11), which act to transfer a phosphate from ATP to the appropriate nucleoside monophosphate. Several schemes for using these enzymes in a detection system are possible in which the four enzymes are immobilized in or near the detection zone of the device. If a constant supply of ATP is introduced into the device and the enzymes are immobilized in parallel, specific phosphorylation can be achieved. Detection can make use of the change in charge or electrophoretic mobility between the nucleoside monophosphate and nucleoside diphosphate.

Alternatively, the binding of the substrate to the enzyme in the detection zone can be used for detection by observing parameters such as migration (e.g., slowed migration of the nucleotide in the zone with the appropriate immobilized enzyme) or spectroscopic properties of the enzyme or substrate. Examples of spectroscopic changes include altered fluorescence excitation or emission wavelengths of tryptophan residues in the enzyme, altered fluorescence lifetimes of tryptophan residues, changes in infrared or Raman spectra, or changes in refractive index at the surface of the device. The enzymes or mutated recombinant enzymes may be labeled with fluorophores which change in fluorescence resonance energy transfer or excimer formation efficiency due to the conformational change induced by nucleotide binding.

The device can be designed and constructed to employ numerous analytical devices to detect and quantify the released reaction products. Analytical techniques using mass spectroscopy can also be incorporated directly into the chemical reaction device to detect released nucleotide monophosphates.

Another class of enzymes which can be used in biosensor applications are the nucleoside kinases (deoxycytidine kinase EC 2.7.1.74, deoxythymidine kinase EC 2.7.1.75 and deoxyadenosine kinase EC 2.1.7.76). In the presence of ADP, these enzymes can specifically catalyze the reverse of their physiological reactions to produce the nucleoside and ATP, which can be assayed by standard methods such as chemiluminescence using firefly luciferase.

Another embodiment combines the reaction and detection processes into the same zone, thus eliminating the need for spatial separation of the retested reaction products (e.g., nucleotide monophosphates) following each cycle. Dye molecules that have different emission spectra following release from the DNA polymer (i.e., the different emissions of polymeric and monomeric fluorescence) can be used in this embodiment. Examples of detection techniques include, but are not limited to, fluorescent polarization and resonance energy transfer. The advantages of a single zone embodiment include the capacity for massively parallel sequencing strategies to be designed and devices constructed for the practice of these strategies. A device capable of performing multiple processes can enhance the reproducibility of sequencing results by querying the degree of synchronism obtained at each cycle. Signal processing software algorithms can be developed to filter out data from non-synchronous read frames.

The digestion of DNA by an exonuclease in an electric field can require careful selection or design of the exonuclease to minimize perturbation due to the electric field. In general, therefore, an enzyme of net neutral charge is most suitable for use in an electric field.

An exonuclease having a net negative charge can be converted to an enzyme of net neutral charge by mutation of surface carboxylate residues (e.g., aspartic acid or glutamic acid) to non-charged, polar groups such as glutamine, asparagine, serine, or threonine. An enzyme having a net charge of −2 may be mutated to have a net neutral charge by replacing a carboxylate residue with a positively charge residue, such as lysine or arginine.

Enzymes of net positive charge may similarly be mutated to an enzyme of net neutral charge by replacing positively charged residues on the surface of the protein with negative or neutral residues.

An electric field can promote dissociation of metal ions (such as $Mg^{++}$) from the enzyme. To avoid any adverse effects of magnesium dissociation, a magnesium-independent enzyme (e.g., some acid exonucleases, venom exonucleases, or phosphodiesterases) can be used. Alternatively, the reaction area can be continuously supplied with magnesium ions.

Polypeptide Sequencing

Polypeptides can be sequenced by using proteolytic enzymes such as the exopeptidases aminopeptidase M (EC 3.4.11.2), and carboxypeptidases A, B, and C (3.4.17.1, EC 3.4.17.2, and EC 3.4.16.1, respectively). The only requirement of a suitable peptidase is broad specificity. Serine-type carboxypeptidase C (EC 3.4.16.5), for example, is a hydrolase that acts on peptide bonds to release the carboxy terminal amino acid residue from any polypeptide. The enzyme has an optimal operating pH range of 4.5 to 6.0. Thus, amino acid residue hydrolysis can be controlled via pressure cycling of pressure-sensitive buffers. Alternatively, the enzymes can simply be inactivated by high pressure in the absence of a buffer having a large ionization volume.

In general, the amino terminal end of a polypeptide chain can be immobilized on a solid support, a hydrolytic peptidase can be introduced under inhibitory pressure conditions, and the pressure can be cycled to release one amino acid residue at a time. Detection schemes as described above in connection with nucleic acid sequencing can also be employed for detection of the free amino acid residues.

The invention will be further described in the following examples, which do not limit the scope of the invention described in the claims.

EXAMPLES

Example One

Preparation of immobilized nucleic acid molecules: Using a Hamilton syringe, a fine-tipped needle is inserted to the midpoint of the internal lumen of a glass capillary tube (e.g., borosilicate or quartz glass for capillary electrophoresis, internal diameter 0.5 mm, length 10 mm). A small volume of a chemical linker (e.g., silanes) in an appropriate solvent is slowly injected into the capillary tube to obtain a band of less than 0.1 mm. Examples of suitable chemical linkers are found in *Nucleic Acid Research* 22:5456–5465, 1994, including various aminosilanes. The linker is attached to a spacer (e.g., glutaraldehyde, 1,4-phenylene-di (isothiocyanate), or succinimidyl-1,4-[maleimidophenyl] butyrate) and a hybridization sequence.

Either a single strand oligonucleotide complementary to a tail of another double stranded nucleic acid molecule to be sequenced or a chemically modified double stranded DNA molecule is chemically coupled to the linker. A nucleic acid molecule with a single strand tail having fluorescently tagged bases is added. The product is then washed both with ethylenediaminetetraacetic acid (EDTA) buffer to remove metal ions and with bovine serum albumin (BSA) to block non-specific binding sites on the capillary tube. A buffered, pH-inhibitory, metal-free solution of exonuclease is added to effect association with the nucleic acid molecule. The mixture is washed to remove unbound exonuclease molecules.

Preparation of the device: An electrode is inserted into one end of the capillary tube. Enzyme-inhibiting buffer solution is slowly injected with a Hamilton syringe to cover the immobilized DNA/enzyme complex. An enzyme activation buffer solution is then slowly injected to form a layer on top of the inhibiting solution. A second electrode is inserted into the other end of the capillary.

Insertion of the device into a high pressure cell: The terminals of a DC power supply are connected to the electrodes at the ends of the capillary. The entire device is carefully inserted into a fluid-filled high pressure cell with pressure-resistant, optical quartz glass; alternatively, fiber optics or a sapphire optical window material can be used with the high pressure cell. The device is oriented to allow spectral detection between the DNA band and the negative electrode (cathode). The optical detection zone is adjacent to the DNA band to enable discrimination between released bases. The electrodes are connected to the power supply, affording external control of current.

Activation of enzyme: The pressure is increased from atmospheric to 50,000 psi. A current at 100 V is applied to the device. The pH of the DNA/enzyme complex changes from inhibitory pH level (e.g., pH 6.0) to permissive pH level (e.g., pH 9.4). After an appropriate time interval (as determined in previous optimization experiments), pressure cycling between 40,000 and 10,000 psi is begun, modulating enzyme activity. The voltage drop is maintained throughout the procedure.

Detection of released nucleotide monophosihates: As the pressure is lowered to permissive levels the exonuclease is activated and the nucleotide monophosphate product is released. The current across the capillary tube allows the temporarily and spatially separated nucleotides tagged with fluorescent dyes to enter the detector zone in a sequential manner.

The resulting data can be expressed as a continuous signal, with intermittent peaks and troughs representing the presence or absence of each of the nucleotide monophosphates. Conventional signal processing algorithms, such as those used with automated gel electrophoresis DNA sequencing instrumentation, can determine the extent of homogeneity of a signal generated in the previous degradation cycle. For example, if multiple DNA molecules from a heterozygotic allele were sequenced, the resultant signal would be a mixture of two bases at one position. Heterogenous sequence results would also be expected when microbiological samples were sequenced (e.g., viral typing of HIV pathogens).

Example Two

Pressure Stimulated Release of a terminal 2-aminopurine 2'-deoxyribonucleoside 5'-monophsophate from duplex DNA: Complementary synthetic oligodeoxynucleotides were purchased from Midland Certified Reagent Company (5'phosphoryl-2-aminopurine-ATA TTA TAT GAG TGT CCT GCA GCA CG and CGT GCT GCA GGA CAC TCA TAT AAT ATT; SEQ ID NOS:1,2).

The oligonucleotides were dissolved in 10 mM Tris at pH 8/100 mM KCl and hybridized by combining equimolar amounts of the oligonucleotides, placing the reaction tube in boiling water, and allowing it to slowly cool to room temperature. The concentration of duplex DNA was 78.3 $\mu$M. This was diluted 1:10 in 10 mM Tris (pH 8)/1 mM EDTA to make a 7.8 $\mu$M stock.

The exonuclease reaction was initiated by the addition of 2.5 $\mu$l of $\lambda$-exonuclease (2.9 units/$\mu$l; Life Technologies) to 211 $\mu$l of water, 25 $\mu$l of 670 mM glycine, pH 9.4 with 500 $\mu$g/ml of BSA and 4 $\mu$l of the 7.8 $\mu$M double-stranded DNA substrate at 292 K. The reaction mixture was transferred to a semi-micro quartz cuvette (Starna Cells) for fluorescence detection and completely topped-off with Dow-Corning silicone high vacuum grease. The top quarter of the cuvette was wrapped with two layers of PARAFILMO® (American National Can) and two layers of DURA-SEALO® (Diversified Biotech).

The cuvette was placed in a custom-built holder and lowered into an ISS high pressure optical bomb which had been filled with spectroscopic grade ethanol. The bomb was sealed with a torque wrench set to 50 ft-lbs and the bomb was placed in an ISS PC1 fluorometer. Pressure was applied by attaching a hand-cranked pressure generator (High Pressure Equipment) and monitored with a digital pressure gauge (Sensotech). Fluorescence was monitored at an excitation wavelength of 311 nm and an emission wavelength of 380 nm.

Pressure stimulation of base release was observed as an increase in the slope of the fluorescence intensity over time. The natural logarithm of the ratio of slope at 14, 5,000, and 10,000 psi to the slope of atmospheric pressure was determined then multiplied by RT (351860/ml psi/mol).

| Pressure (psi) | RTln (rate[p]/rate[atm]) |
|---|---|
| 14 | 0 |
| 5000 | 174727 |
| 10000 | 300312 |

This log ratio was plotted against the pressure. The slope was determined using the SigmaPlot software and multiplied by R·T (R=1205 (ml·psi)/(mol·K) and T=292 K) to yield a slope of −31+/−3 ml/mol., indicating that the reaction is strongly stimulated by pressure.

Example 3

A detection scheme based on fluorescence resonance energy transfer (FRET) between fluoroyhores on the enzyme and on the DNA: Fluorescence resonance energy transfer (FRET) is a spectroscopic phenomenon in which two fluorophores will interact in such a way that when one fluorophore is excited by light, it will transfer energy to another nearby (about 5 to 100 Å) fluorophore having an excitation spectrum that overlaps with the emission spectrum of the first fluorophore. The second fluorophore will then emit light at a longer wavelength than would have been emitted by the first fluorophore alone. The energy transfer is highly specific for closely positioned fluorophores since it decreases proportionally to the sixth power of the distance between the two fluorophores.

FRET can be used to eliminate the need for separation of the product nucleotides from the oligomeric substrate normally required by nucleotide detection and discrimination methods. The native fluorescence of groups on the enzyme such as tryptophan, tyrosine and phenylalanine can donate energy to labels on the DNA or the enzyme can be tagged with a non-native fluorophore. The nucleotides can be discriminated by using four different fluorescent tags, each emitting at a characteristic wavelength or by using a mixture of enzymes tagged with fluorophores that excite at different wavelengths and tagged nucleotides that are excited by these tagged enzymes. Alternatively, the labels on the DNA can donate energy to the label or labels on the enzyme.

Example 4

Pressure-modulated hydrolysis and product release: A linearized, double strand DNA sample to be sequenced is covalently immobilized on a solid support in a sequencing device. Exonuclease III in introduced in excess to associate with the DNA sample. The enzyme is in a buffer solution containing a pressure-sensitive buffer having a large ionization volume. At atmospheric pressure, the pH of the buffer is inhibitory for Exonuclease III's hydrolytic activity. The pH is, however, permissive for association and binding of the enzyme with the DNA sample.

The DNA is chemically coupled to a solid support contained within an alternating or continuous electromotive potential. By introducing the enzyme bound to the DNA, the DNA molecule becomes oriented adjacent to a detector zone. The detector zone is an optically clear region of the sequencing device, in which laser-induced fluorescent excitation and emission of nucleotide monophosphates can be monitored.

The pressure is increased to a hydrolytically permissive zone, which inhibits product release. The pressure is then decreased to a product release permissive zone, which inhibits hydrolysis. The pressure is cycled, alternating between these limiting zones, while concurrently removing the products from the reaction vessel electrophoretically. The sequence can thus be read in real-time (i.e., as the individual nucleotides are being hydrolyzed away from the immobilized molecule. When the hydrolysis and product release steps reach their respective end-points at the end of each pressure cycle, resynchronization of the enzymes occurs, such that all of the enzymes rest on a common base when the pressure is non-permissive.

Example 5

Coupling of a DNA molecule to a glass plate: To immobilize a polymeric biomolecule on a solid support, it is generally necessary to chemically modify one end of the molecule with a reactive functional group. Suitable functional groups include primary amine and thiols. For small DNA molecules (e.g., less than 40 nucleotides), automated DNA synthesizing equipment that uses phosphoramidite compounds can be used to functionalized the end of the DNA. The polymerase chain reaction (PCR) can be used to activate larger DNA molecules (i.e., 80–1000 nucleotides).

The forward primer of the LACZ gene was obtained and modified to include a primary amino group at its 5' end. This primer was used to 5' modify an 800-bp DNA molecules in the PCR reaction.

The 800-bp, double-stranded DNA molecule was then labelled with a fluorescent reporter by partial substitution of dTTP with fluorescein-labelled dUTP (New England Nuclear, DuPont, Wilmington, Del.), also via PCR.

After incorporation of the fluorescent label, glass plates were prepared for DNA attachment. 25×75 mm glass slides were cleaned with a 1:2 solution of 30% aqueous hydrogen peroxide and 98% sulfuric acid. Cleaning in this manner creates a hydrophilic surface on the slides and exposes SiO-ions on the surface. The slides were then dried at 120° C. for 10 minutes.

The cleaned and dried plates were treated with 3-aminopropyltriethoxysilane (APTES), a silanization reagent that modifies the glass to incorporate a terminal amino group (*Nucleic Acid Research*, 24:3031-3039, 1996). A 1% APTES solution in 95% denatured methanol was used; the glass was dipped in the solution for 20 minutes at room temperature. After silanization, the water contact angle of the glass had increased from 0° to 36°.

The APTES-coated glass was further activated with glutaraldehyde, which acts as a linker between the aminemodified DNA molecule and the amine-modified glass. Thus, the silanized plates were treated with a 12.5% (v/v) solution of glutaraldehyde (Sigma, St. Louis, Mo.) in coupling buffer (0.1 M sodium phosphate/0.15 M sodium chloride, pH 7.0) with 0.6 g sodium cyanoborohydride per 100 ml of coupling buffer. The glutaraldehyde-activated plates were washed two more times with the coupling buffer.

The fluoroscein-labelled PCR product with the 5'-primary amine linker and the glutaraldehyde-activated plates were incubated together overnight in coupling buffer to allow diffusion and reaction of DNA molecules at the solid-liquid interface. The slide was washed with coupling buffer and 0.1 M tris buffer (pH 8), then imaged under an epi-fluorescence microscope at 470–490 nm as a-light source for fluorescein excitation. Four distinct bright spots with green light emission were observed.

Thus, the amine-modified, 800-bp PCR product was concluded to have been coupled to the glutaraldehyde-activated glass. Further washing of the plate with distilled water did not significantly reduce the fluorescence intensity, consistent with covalent binding.

Example 6

Radial electro-analytical DNA sequencing device: Three silicon substrates are etched to form plates each having circular microstructures of 40 μm in diameter. Circular rings of two different sizes are also etched onto each of the plates, the first having an outer diameter of 120 μm and an inner diameter of 40 μm, and the second having an outer diameter of 200 μm and an inner diameter of 120 μm.

Three photo-resist polymer stamps with uniform, 200 μm circles and the first and second circular rings described above, respectively, are developed from the etched silicon substrates.

The polymer stamps are soaked with different solvents to pattern a cleaned glass surface with surface active reagents including different silanes. Thus, the first polymer resist (i.e., having 40 μm circles) is soaked with 2% (v/v) 3-amino-triethoxysilane (APTES) in 95% methanol, then used to pattern a predetermined region of the glass surface. The second polymer stamp (i.e., having the first circular ring) is soaked in 0.6% (v/v) APTES in 95% methanol and used to pattern the same region on glass and subsequently with 1% dimethyl-dichlorosilane (DCS) in 100% trichloromethane. DCS acts as a capping agent for the APTES silanized glass and increases the surface hydrophobicity in the region. The third surface polymer-resist stamp is patterned with the second circular ring in 2% APTES cosolvent. Thus, concentric circles with three distinct surface properties are made on the glass surface. Amino-modified DNA molecules are coupled to the mixed silanized region of APTES and DCS with the second concentric ring polymer stamp to form polymer brushes.

By inserting a micro-electrode of negative charge in the center of the concentric micro-structure and a circular electrode with a diameter of 200 $\mu$m to surround the circle, a radial DNA sequencing device is made. The device is used to enzymatically digest DNA in the hydrophobic region of the first ring and detect the individual nucleotide in the hydrophilic region of the second ring under the rapid pressure cycling conditions in the presence of a radial electric field. This micro-patterning method can allow parallel sequencing of thousands of DNA samples.

Other Embodiments

It is to be understood that while the invention has been described in conjunction with the detailed description thereof, that the foregoing description is intended to illustrate and not to limit the scope of the appended claims. Other aspects, advantages, and modifications are within the scope of the following claims.

What is claimed is:

1. An integrated device for sequencing a polymeric biomolecule, the device comprising:
    a reaction vessel, wherein said reaction vessel includes a reaction zone and a detection zone;
    a solid support in said reaction zone for chemical attachment of the polymeric biomolecule;
    an enzyme that catalyzes the removal of one monomer unit at a time from a terminus of said polymeric biomolecule;
    a probe for sensing a characteristic of monomers positioned within the detection zone of the reaction vessel; and
    a pressure-control device that controls the pressure at least in the reaction zone of said reaction vessel, wherein said probe comprises an optical window of quartz or sapphire.

2. An integrated device for sequencing a polymeric biomolecule, the device comprising:
    a reaction vessel, wherein said reaction vessel includes a reaction zone and a detection zone, wherein said reaction zone is spatially separated from said detection zone;
    a solid support in said reaction zone for chemical attachment of the polymeric biomolecule;
    an enzyme that catalyzes the removal of one monomer unit at a time from a terminus of said polymeric biomolecule;
    a probe for sensing a characteristic of monomers positioned within the detection zone of the reaction vessel;
    a pressure-control device that controls the pressure at least in the reaction zone of said reaction vessel; and
    a electrophoretic or electroosmotic device connecting said reaction and detection zones, wherein said modulated device contains a buffer, the pH of the buffer being pressure-sensitive.

* * * * *